US008642754B2

(12) United States Patent
Fujimoto et al.

(10) Patent No.: US 8,642,754 B2
(45) Date of Patent: Feb. 4, 2014

(54) PHOTORESPONSIVE NUCLEIC ACID MANUFACTURING METHOD

(75) Inventors: Kenzo Fujimoto, Nomi (JP); Masayuki Ogino, Nomi (JP); Yoshinaga Yoshimura, Nomi (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 374 days.

(21) Appl. No.: 12/867,694

(22) PCT Filed: Feb. 13, 2009

(86) PCT No.: PCT/JP2009/000562
§ 371 (c)(1),
(2), (4) Date: Oct. 25, 2010

(87) PCT Pub. No.: WO2009/101810
PCT Pub. Date: Aug. 20, 2009

(65) Prior Publication Data
US 2011/0040083 A1 Feb. 17, 2011

(30) Foreign Application Priority Data

Feb. 14, 2008 (JP) ................................ 2008-033713

(51) Int. Cl.
*C07H 21/00* (2006.01)
*C07H 21/02* (2006.01)
*C07H 21/04* (2006.01)

(52) U.S. Cl.
CPC ............... *C07H 21/00* (2013.01); *C07H 21/02* (2013.01); *C07H 21/04* (2013.01)
USPC ..................................... 536/25.32; 536/24.3

(58) Field of Classification Search
None
See application file for complete search history.

(56) References Cited

U.S. PATENT DOCUMENTS

2004/0192542 A1    9/2004    Choudary et al.

FOREIGN PATENT DOCUMENTS

| JP | 2000-510145 A | 8/2000 |
| JP | 2001-348398 A | 12/2001 |
| JP | 2004-298802 A | 10/2004 |
| JP | 2004-535193 A | 11/2004 |
| JP | 2005-350386 A | 12/2005 |

OTHER PUBLICATIONS

Yin, Chem. Rev., 2007, 107, 133-173.*
Izuta et al., Chem. Pharm. Bull., 1987, 35, 4829-4838.*
Capek et al., Organic & Biomolecular Chemistry, 2006, 4, 2278-84.*
Agrofoglio et al., Chem. Rev., 2003, 103, 1875-1916.*
Ashida et al., Antiviral Research, 1997, 35, 167-175.*
Phan et al., Tetrahedron Letters, 2004, 45, 7915-7919.*
Yoshinaga Yoshimura et al., "Highly Selective and Sensitive Template-Directed Photoligation of DNA via 5-Carbamoylvinyl-2'-deoxycytidine", Organic Letters, Sep. 2006, 5049-5051, vol. 8 No. 22.
Jonathan L. Sessler et al., "Novel Guanosine-Cytidine Dinucleoside that Self-Assembles into a Trimeric Supramolecule", Organic Letters, Jun. 27, 2003, p. 2627-2630, vol. 5 No. 15.
J. Liu et al., "Synthesis and Antiviral Activities of Some New 5-heteroaromatic Substituted Derivatives of 2'-deoxyuridine", Nucleosides & Nucleotides, May 1995, p. 525-528, vol. 14(3-5).
Donald E. Bergstrom et al., "Pyrrolo[2,3-d] Pyrimidine Nucleoside Antibiotic Analogs. Synthesis via Organopalladium Intermediates Derived from 5-mercuritubercidin", The Journal of Organic Chemistry, Mar. 1981, p. 1423-1431, vol. 46 No. 7.
I. Luyten et al., "2'-Deoxyuridines with a 5-heteroaromatic substituent: synthesis and biological evaluation", Antiviral Chemistry & Chemotherapy, Jul. 1995, p. 262-270, vol. 6 No. 4.
S. Shigeta et al., "Synthesis and antiherpesvirus activities of 5-alkyl-2-thiopyrimidine nucleoside analogues", Antiviral Chemistry & Chemotherapy, Mar. 2002, p. 67-82, vol. 13 No. 2.
Vittorio Farina et al., "The Stille Reaction", Organic Reactions, Apr. 1997, p. 366, vol. 50.
International Search Report of PCT/JP2009/000562, Mailing Date of May 12, 2009.
Notification of Transmittal of Translation of the International Preliminary Report on Patentability ( Form PCT/IB/338) of International Application No. PCT/JP2009/000562 mailed Oct. 14, 2010 with Forms PCT/IPEA/409.
Extended European Search Report dated Aug. 7, 2013, issued in corresponding European Patent Application No. 09710413.7 (5 pages).
Ogino et al., "Effective Synthesis of Photosensitive Oligodeoxynucleotides",Nucleic Acids Symposium Series, vol. 52, Sep. 8, 2008, pp. 395-396; cited in Extended European Search Report dated Aug. 7, 2013.

* cited by examiner

*Primary Examiner* — Eric S Olson
(74) *Attorney, Agent, or Firm* — Westerman, Hattori, Daniels & Adrian, LLP

(57) ABSTRACT

The present invention provides a manufacturing method that can easily manufacture a compound known as photoresponsive (photocoupling) nucleic acids at high yield in a shorter period of time than that of the conventional technology. The present invention relates to a method of manufacturing a photoresponsive nucleic acid which includes a step of reacting a nucleic acid having groups represented by the Formula I, the Formula III, the Formula IV, or the Formula V and a compound represented by the Formula II, or reacting a nucleic acid having groups represented by the Formula VI, the Formula VIII, the Formula IX, or the Formula X and a compound represented by the Formula VII by heating them by microwaves in the presence of a metal catalyst, a basic substance, and a solvent.

9 Claims, 3 Drawing Sheets

$^{CV}U$ $^{CMV}U$ $^{CNV}U$ $^{V}U$

PHOTORESPONSIVE NUCLEIC ACID MANUFACTURING METHOD

TECHNICAL FIELD

The present invention relates to a method of manufacturing a photoresponsive nucleic acid.

BACKGROUND ART

Coupling of nucleic acids is one of the basic techniques in the field of molecular biology. The coupling of nucleic acids is used, for example, for introduction of a gene or detection of a base sequence, in combination with hybridization. For such a reason, coupling of nucleic acids is a very important technique used not only for basic studies in molecular biology but also for diagnosis or therapeutics in medical field, development or production of an agent for therapeutics or an agent for diagnosis, and development or production of an enzyme or a microorganism in the field of engineering and agriculture, for example.

In the related art, coupling of nucleic acids has been carried out by using, for example, a DNA ligase, etc. However, it is disadvantageous in that, for such reaction based on an enzymatic reaction occurring in a living body, a specific condition is required and the enzymes used are relatively expensive and not stable enough, etc. To overcome these disadvantages, a technology of coupling nucleic acids without using enzymes has been studied.

As a technology of coupling nucleic acids without using enzymes, there is a method using an organic compound reactive to a nucleic acid. In recent years, a technique of coupling nucleic acids based on photoreaction has been drawing attention due to the advantages that temporal and spatial control of the reaction is freely achievable and the reaction can be carried out under a mild condition compared to general organic chemistry, etc.

As for such a technique for photocoupling, a photocoupling technique using 5-cyanovinyldeoxyuridine and its derivatives (photocoupling nucleic acids or photoresponsive nucleic acids) is known (Patent Document 1: Japanese Patent No. 3753938 and Patent Document 2: Japanese Patent No. 3753942).

Although these photoresponsive nucleic acids have excellent characteristics, their synthesis is not easy, a long reaction time like several hours to several days is required to obtain a target compound in sufficient amount. In addition, as it is accompanied by a side reaction, yield is not high, i.e., it is only 50% to 60%.

Patent Document 1: Japanese Patent No. 3753938
Patent Document 2: Japanese Patent No. 3753942

DISCLOSURE OF THE INVENTION

Problems to be Solved by the Invention

As described above, the compounds known as photoresponsive (photocoupling) nucleic acids including 5-cyanovinyldeoxyuridine and its derivatives cannot be easily synthesized, have required a long reaction time, and are produced with low yield.

For such reasons, there has been longed for a method of manufacturing a compound known as photoresponsive (photocoupling) nucleic acids by which the compound can be obtained with high yield within a short period of time compared to the conventional technology.

Under the circumstances, an object of the present invention is to provide a method of manufacturing a compound known as photoresponsive (photocoupling) nucleic acids in a simple way within a short period of time with high yield compared to the conventional technology.

In addition, to obtain conventionally a photoresponsive (photocoupling) nucleic acid compound as a derivative in which part of the base in oligodeoxyribonucleotide (ODN) is modified, for example, it has to be prepared by using a DNA synthesizer, etc., starting from a modified nucleoside including base moieties that are modified in advance and undergoing the form of a phosphoroamidite. Specifically, according to the conventional technology, when it is desired to produce photoresponsive nucleic acids having a differently modified base from an oligodeoxyribonucleotide having an identical base sequence, a method of preparing photoresponsive nucleic acids by which an oligodeoxyribonucleotide having a desired base sequence is prepared first and then a desired modification is carried out for the target base to obtain desired photoresponsive nucleic acids (i.e., post-synthetic method) cannot be employed. If it is desired to obtain photoresponsive nucleic acids having a differently modified base, it is necessary to start from a modified nucleoside having base moieties that are modified in advance and, after undergoing the form of a phosphoroamidite, the entire oligodeoxyribonucleotide should be synthesized therefrom each time.

For such reasons, a method of preparing photoresponsive nucleic acids by which an oligodeoxyribonucleotide having a desired base sequence is prepared and a desired modification is carried out for the target base whenever it is desired (i.e., post-synthetic method) has been needed.

Thus, the another object of the present invention is to provide a method of producing a compound known as photoresponsive (photocoupling) nucleic acids by which an oligodeoxyribonucleotide having a desired base sequence is prepared and then a desired modification is carried out for the target base whenever it is desired to obtain the desired photoresponsive nucleic acids.

Means for Solving the Problems

As a result of extensive studies regarding a method of manufacturing a photoresponsive nucleic acid, inventors of the present invention found that the objects described above can be accomplished by the manufacturing method described below, and therefore completed the invention.

Accordingly, the present invention is directed to the following [1] to [16].

[1] A method of manufacturing photoresponsive nucleic acids (the nucleic acids include a nucleic acid, a mononucleotide and a peptide nucleic acid) comprising the following step (a):

(a) nucleic acids (the nucleic acids include a nucleic acid, a mononucleotide and a peptide nucleic acid) having a group represented by the Formula I, the Formula III, the Formula IV or the Formula V as a base moiety:

[Chemical Formula 1]

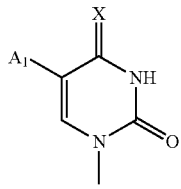
(I)

(in the Formula I, X represents O, S or NH, and
A1 represents a halogen atom.)

[Chemical Formula 2]

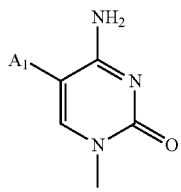
(III)

(in the Formula III, A1 represents a halogen atom.)

[Chemical Formula 3]

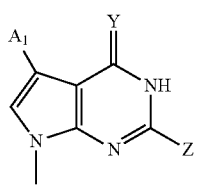
(IV)

(in the Formula IV, Y represents O, S or NH,
Z represents $NH_2$ when Y is O or S, or a hydrogen atom when Y is NH, and
A1 represents a halogen atom.)

[Chemical Formula 4]

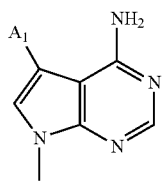
(V)

(in the Formula V, A1 represents a halogen atom.)
are reacted with the compound that is represented by the following Formula II:

[Chemical Formula 5]

(II)

(in the Formula II, R1 represents a hydrogen atom, a cyano group, a carboxamide group, an alkoxycarbonyl group, or a monovalent group of a substituted or unsubstituted aromatic compound, and R2 represents a hydrogen atom, a C1 to C6 alkyl group, a C1 to C6 alkoxy group, a cyano group or a C1 to C6 acyl group.)

in the presence of a metal catalyst, a basic substance and a solvent by microwave heating, or the following step (b):

(b) nucleic acids (the nucleic acids include a nucleic acid, a mononucleotide and a peptide nucleic acid) having a group represented by the Formula VI, the Formula VIII, the Formula IX or the Formula X as a base moiety:

[Chemical Formula 6]

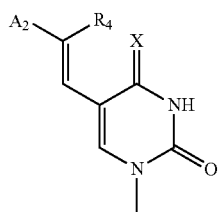
(VI)

(in the Formula VI, X represents O, S or NH,

R4 represents a hydrogen atom, a C1 to C6 alkyl group, a C1 to C6 alkoxy group, a cyano group or a C1 to C6 acyl group, and A2 represents a halogen atom.)

[Chemical Formula 7]

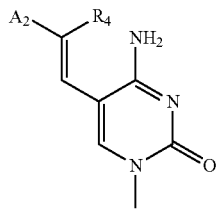
(VIII)

(in the Formula VIII, R4 represents a hydrogen atom, a C1 to C6 alkyl group, a C1 to C6 alkoxy group, a cyano group or a C1 to C6 acyl group, and A2 represents a halogen atom.)

[Chemical Formula 8]

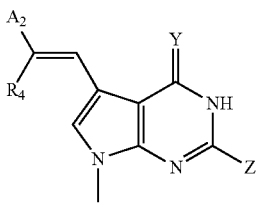
(IX)

(in the Formula IX, Y represents O, S or NH,
Z represents NH$_2$ when Y is O or S, or a hydrogen atom when Y is NH,
R4 represents a hydrogen atom, a C1 to C6 alkyl group, a C1 to C6 alkoxy group, a cyano group or a C1 to C6 acyl group, and
A2 represents a halogen atom.)

[Chemical Formula 9]

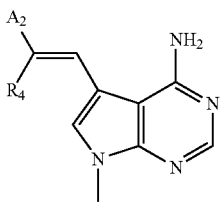
(X)

(in the Formula X, R4 represents a hydrogen atom, a C1 to C6 alkyl group, a C1 to C6 alkoxy group, a cyano group or a C1 to C6 acyl group, and
A2 represents a halogen atom.)
are reacted with the compound that is represented by the following Formula VII:

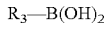
R$_3$—B(OH)$_2$  (VII)

(in the Formula VII, R$_3$ represents a monovalent group of a substituted or unsubstituted aromatic compound, a hydrogen atom, a cyano group, a carboxamide group or an alkoxycarbonyl group.)
in the presence of a metal catalyst, a basic substance and a solvent by microwave heating.

[2] The method according to [1], comprising the step (a).
[3] The method according to [1], comprising the step (b).
[4] The method according to [1] or [2], wherein the photoresponsive nucleic acids that are manufactured by the step (a) are the photoresponsive nucleic acids which include the following groups that are represented by the Formula XI, the Formula XII, the Formula XIII or the Formula XIV:

[Chemical Formula 10]

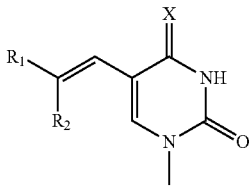
(XI)

(in the Formula XI, X represents O, S or NH,
R1 represents a hydrogen atom, a cyano group, a carboxamide group, an alkoxycarbonyl group, or a monovalent group of a substituted or unsubstituted aromatic compound, and
R2 represents a hydrogen atom, a C1 to C6 alkyl group, a C1 to C6 alkoxy group, a cyano group or a C1 to C6 acyl group.)

[Chemical Formula 11]

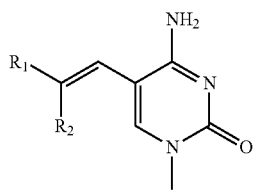
(XII)

(in the Formula XII, R1 represents a hydrogen atom, a cyano group, a carboxamide group, an alkoxycarbonyl group, or a monovalent group of a substituted or unsubstituted aromatic compound, and
R2 represents a hydrogen atom, a C1 to C6 alkyl group, a C1 to C6 alkoxy group, a cyano group or a C1 to C6 acyl group.)

[Chemical Formula 12]

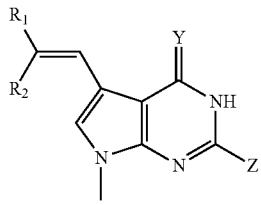
(XIII)

(in the Formula XIII, Y represents O, S or NH,
Z represents NH$_2$ when Y is O or S, or a hydrogen atom when Y is NH,
R1 represents a hydrogen atom, a cyano group, a carboxamide group, an alkoxycarbonyl group, or a monovalent group of a substituted or unsubstituted aromatic compound, and
R2 represents a hydrogen atom, a C1 to C6 alkyl group, a C1 to C6 alkoxy group, a cyano group or a C1 to C6 acyl group.)

[Chemical Formula 13]

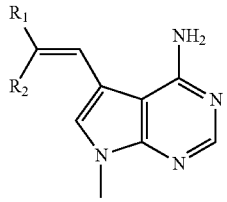
(XIV)

(in the Formula XIV, R1 represents a hydrogen atom, a cyano group, a carboxamide group, an alkoxycarbonyl group, or a monovalent group of a substituted or unsubstituted aromatic compound, and
R2 represents a hydrogen atom, a C1 to C6 alkyl group, a C1 to C6 alkoxy group, a cyano group or a C1 to C6 acyl group.) (the group represented by the Formula XI is produced from a reaction between the groups that are represented by the Formula I and the Formula II, the group represented by the Formula XII is produced from a reaction between the groups that are represented by the Formula III and the Formula II, the group represented by the Formula XIII is produced from a reaction between the groups that are represented by the Formula IV and the Formula II, and the group represented by the Formula XIV is produced from a reaction between the groups that are represented by the Formula V and the Formula II, respectively).

[5] The method according to [1] or [3], wherein the photoresponsive nucleic acids that are manufactured by the step (b) are the photoresponsive nucleic acids which include the following groups that are represented by the Formula XV, the Formula XVI, the Formula XVII or the Formula XVIII:

[Chemical Formula 14]

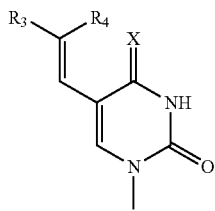

(XV)

(in the Formula XV, X represents O, S or NH,

R4 represents a hydrogen atom, a C1 to C6 alkyl group, a C1 to C6 alkoxy group, a cyano group or a C1 to C6 acyl group, and R3 represents a monovalent group of a substituted or unsubstituted aromatic compound, a hydrogen atom, a cyano group, a carboxamide group or an alkoxycarbonyl group.)

[Chemical Formula 15]

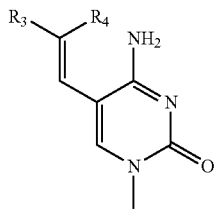

(XVI)

(in the Formula XVI, R4 represents a hydrogen atom, a C1 to C6 alkyl group, a C1 to C6 alkoxy group, a cyano group or a C1 to C6 acyl group, and R3 represents a monovalent group of a substituted or unsubstituted aromatic compound, a hydrogen atom, a cyano group, a carboxamide group or an alkoxycarbonyl group.)

[Chemical Formula 16]

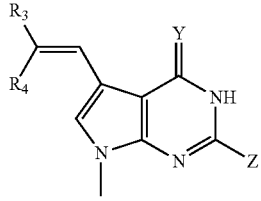

(XVII)

(in the Formula XVII, Y represents O, S or NH,

Z represents $NH_2$ when Y is O or S, or a hydrogen atom when Y is NH,

R4 represents a hydrogen atom, a C1 to C6 alkyl group, a C1 to C6 alkoxy group, a cyano group or a C1 to C6 acyl group, and R3 represents a monovalent group of a substituted or unsubstituted aromatic compound, a hydrogen atom, a cyano group, a carboxamide group or an alkoxycarbonyl group.)

[Chemical Formula 17]

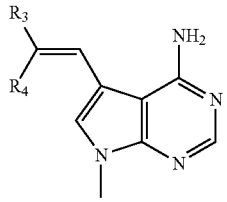

(XVIII)

(in the Formula XVIII, R4 represents a hydrogen atom, a C1 to C6 alkyl group, a C1 to C6 alkoxy group, a cyano group or a C1 to C6 acyl group, and R3 represents a monovalent group of a substituted or unsubstituted aromatic compound, a hydrogen atom, a cyano group, a carboxamide group or an alkoxycarbonyl group.) (the group represented by the Formula XV is produced from a reaction between the groups that are represented by the Formula VI and the Formula VII, the group represented by the Formula XVI is produced from a reaction between the groups that are represented by the Formula VIII and the Formula VII, the group represented by the Formula XVII is produced from a reaction between the groups that are represented by the Formula IX and the Formula VII, and the group represented by the Formula XVIII is produced from a reaction between the groups that are represented by the Formula X and the Formula VII, respectively).

[6] The method according to [9], [2] or [4], wherein the step (a) is carried out by heating by microwaves in the presence of a metal catalyst, a basic substance, a solvent and a substance for activating the reaction.

[7] The method according to [1], [3] or [5], wherein the step (b) is carried out by heating by microwaves in the presence of a metal catalyst, a basic substance, a solvent and a substance for activating the reaction.

[8] The method according to any one of [1] to [7], wherein the metal catalyst is a palladium complex catalyst.

[9] The method according to any one of [1] to [8], wherein the solvent is an aprotic polar solvent.

[10] The method according to any one of [1] to [9], wherein the basic substance is trialkylamine having a C1 to C6 alkyl group.

[11] The method according to any one of [6] to [10], wherein the substance for activating the reaction is an aqueous solution of carboxylate.

[12] The method according to any one of [6] to [11], wherein the aqueous solution of carboxylate is used both as a basic substance and a substance for activating the reaction.

[13] The method according to [11] or [12], wherein the aqueous solution of carboxylate is an aqueous solution of an alkali metal salt of C1 to C3 carboxylic acid.

[14] The method according to any one of [11] to [13], wherein the aqueous solution of carboxylate is a buffer solution having a pH range of 4.5 to 6.0.

[15] The method according to any one of [1] to [14], wherein the heating by microwaves is carried out in the temperature range of 70 to 140° C.

[16] The method according to any one of [1] to [15], wherein the heating by microwaves is carried out in the time range of 1 to 30 minutes.

Furthermore, the present invention is also directed to the following [17] to [21].

[18] The method of manufacturing a photoresponsive base, wherein, in the step (a), a compound consisting of a group represented by Formula I, Formula III, Formula IV or Formula V and a hydrogen atom bonded thereto are caused to reach with a compound represented by Formula II to give a photoresponsive base consisting of a group represented by Formula XI, Formula XII, Formula XIII or Formula XIV and a hydrogen atom bonded thereto.

[19] The method of manufacturing a photoresponsive base, wherein, in the step (b), a compound consisting of a group represented by Formula VI, Formula VIII, Formula IX or Formula X and a hydrogen atom bonded thereto are caused to react with a compound represented by Formula VII to give a photoresponsive base consisting of a group represented by Formula XV, Formula XVI, Formula XVII or Formula XVIII and a hydrogen atom bonded thereto.

[20] The method of manufacturing a photoresponsive nucleoside or its derivative, wherein, in the step (a), a nucleoside having a group represented by Formula I, Formula III, Formula IV or Formula V as a base moiety or its derivative is caused to react with a compound represented by Formula II to give a photoresponsive nucleoside represented by Formula XI, Formula XII, Formula XIII or Formula XIV or its derivative.

[21] The method of manufacturing a photoresponsive nucleoside or its derivative, wherein, in the step (b), a nucleoside having a group represented by Formula VI, Formula VIII, Formula IX or Formula X as a base moiety or its derivative is caused to react with a compound represented by Formula VII to give a photoresponsive nucleoside represented by Formula XV, Formula XVI, Formula XVII or Formula XVIII or its derivative.

Effects of the Invention

According to the present invention, a compound known as photoresponsive (photocoupling) nucleic acids can be obtained with higher yield within a shorter time than that of the conventional technology. For example, regarding the synthesis of a monomer of photoresponsive nucleic acids, the reaction can be completed within several minutes compared to several hours required by the method of conventional technology. Furthermore, the yield is also increased by several tens of percent than before, and therefore manufacturing with favorable efficiency in every aspect can be carried out.

Furthermore, when obtaining conventionally a photoresponsive (photocoupling) nucleic acid compound, for example, as a derivative in which part of the base in oligodeoxyribonucleotide (ODN) is modified, it has to start from a modified nucleoside including base moieties that are modified in advance, then the modified nucleoside is rendered into the form of a phosphoroamidite. In addition, it has to be prepared by using a DNA synthesizer, etc. Specifically, when it is desired to produce photoresponsive nucleic acids having a differently modified base from an oligodeoxyribonucleotide having an identical base sequence, a method of preparing photoresponsive nucleic acids by which an oligodeoxyribonucleotide having a desired base sequence is prepared first and then a desired modification is carried out for the target base to obtain desired photoresponsive nucleic acids (i.e., post-synthetic method) cannot be employed. If it is desired to obtain photoresponsive nucleic acids having a differently modified base, it is necessary to start from a modified nucleotide having base moieties that are modified in advance and, the modified nucleotide is rendered into the form of a phosphoroamidite, and the entire oligodeoxyribonucleotide should be synthesized therefrom each time.

On the other hand, the present invention is to provide for the first time a method of providing a desired photoresponsive nucleic acids by which an oligodeoxyribonucleotide having a desired base sequence is prepared and then a desired modification is carried out for the target base whenever it is desired (i.e., post-synthetic method).

According to the post-synthetic method of the present invention, an oligomer of photoresponsive nucleic acids may be manufactured in a day, which requires a week to prepare according to the conventional synthetic method based on a phosphoroamidite method. Further, since it has very high yield, an innovative manufacturing method with favorable efficiency in every aspect is provided for the first time by the invention.

BEST MODE FOR CARRYING OUT THE INVENTION

Figure 1:
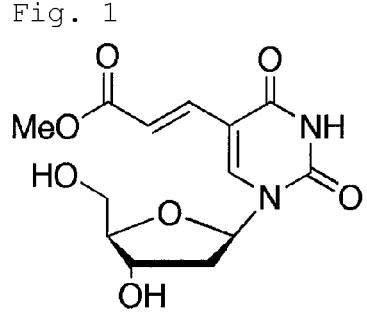
FIG. 1 is a drawing showing the structural formula of $^{CV}U$.

Herein below, the present invention is explained in detail in view of specific embodiments. However, the present invention is not limited to the specific embodiments that are given below as an example.

The present invention relates to a method of manufacturing photoresponsive nucleic acids including the following step (a):

(a) nucleic acids (the nucleic acids include a nucleic acid, a mononucleotide and a peptide nucleic acid) having a group represented by the Formula I, the Formula III, the Formula IV or the Formula V as a base moiety:

[Chemical Formula 18]

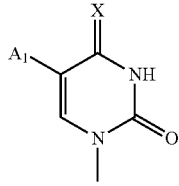
(I)

(in the Formula I, X represents O, S or NH, and
A1 represents a halogen atom.)

[Chemical Formula 19]

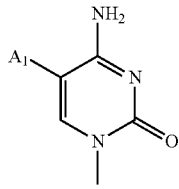
(III)

(in the Formula III, A1 represents a halogen atom.)

[Chemical Formula 20]

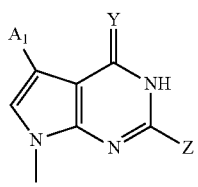
(IV)

(in the Formula IV, Y represents O, S or NH,
Z represents $NH_2$ when Y is O or S, or a hydrogen atom when Y is NH, and
A1 represents a halogen atom.)

[Chemical Formula 21]

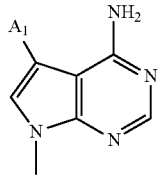
(V)

(in the Formula V, A1 represents a halogen atom.)

are reacted with the compound that is represented by the following Formula II:

[Chemical Formula 22]

(II)

(in the Formula II, R1 represents a hydrogen atom, a cyano group, a carboxamide group, an alkoxycarbonyl group, or a monovalent group of a substituted or unsubstituted aromatic compound, and R2 represents a hydrogen atom, a C1 to C6 alkyl group, a C1 to C6 alkoxy group, a cyano group or a C1 to C6 acyl group.)

in the presence of a metal catalyst, a basic substance and a solvent by microwave heating, or the following step (b):

(b) nucleic acids (the nucleic acids include a nucleic acid, a mononucleotide and a peptide nucleic acid) having a group represented by the Formula VI, the Formula VIII, the Formula IX or the Formula X as a base moiety:

[Chemical Formula 23]

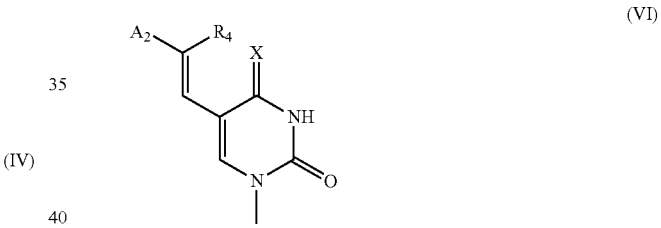
(VI)

(in the Formula VI, X represents O, S or NH,

R4 represents a hydrogen atom, a C1 to C6 alkyl group, a C1 to C6 alkoxy group, a cyano group or a C1 to C6 acyl group, and A2 represents a halogen atom.)

[Chemical Formula 24]

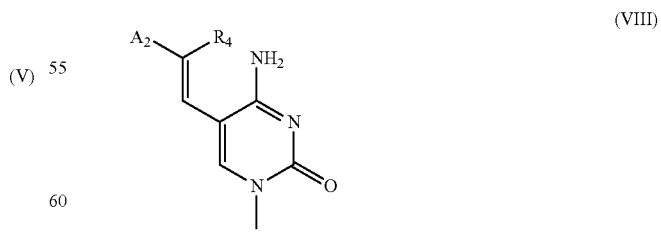
(VIII)

(in the Formula VIII, R4 represents a hydrogen atom, a C1 to C6 alkyl group, a C1 to C6 alkoxy group, a cyano group or a C1 to C6 acyl group, and A2 represents a halogen atom.)

[Chemical Formula 25]

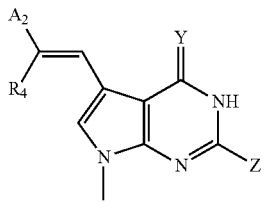

(IX)

(in the Formula IX, Y represents O, S or NH,
Z represents $NH_2$ when Y is O or S, or a hydrogen atom when Y is NH,
R4 represents a hydrogen atom, a C1 to C6 alkyl group, a C1 to C6 alkoxy group, a cyano group or a C1 to C6 acyl group, and
A2 represents a halogen atom.)

[Chemical Formula 26]

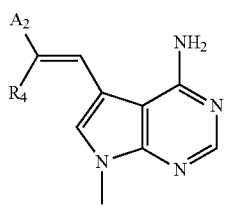

(X)

(in the Formula X, R4 represents a hydrogen atom, a C1 to C6 alkyl group, a C1 to C6 alkoxy group, a cyano group or a C1 to C6 acyl group, and
A2 represents a halogen atom.)
are reacted with the compound that is represented by the following Formula VII:

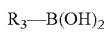 (VII)

(in the Formula VII, R3 represents a monovalent group of a substituted or unsubstituted aromatic compound, a hydrogen atom, a cyano group, a carboxamide group or an alkoxycarbonyl group.)
in the presence of a metal catalyst, a basic substance and a solvent by microwave heating.

By using the method described above, the present invention provides a method of manufacturing photoresponsive nucleic acids including the following groups that are represented by Formula XI, Formula XII, Formula XIII or Formula XIV as photoresponsive nucleic acids that are produced according to step (a):

[Chemical Formula 27]

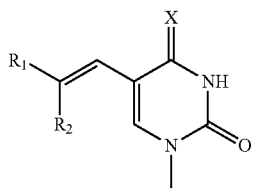

(XI)

(in Formula XI, X represents O, S or NH, R1 represents a hydrogen atom, a cyano group, a carboxamide group, an alkoxycarbonyl group, or a monovalent group of a substituted or unsubstituted aromatic compound, and R2 represents a hydrogen atom, a C1 to C6 alkyl group, a C1 to C6 alkoxy group, a cyano group or a C1 to C6 acyl group.)

[Chemical Formula 28]

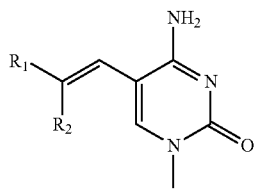

(XII)

(in Formula XII, R1 represents a hydrogen atom, a cyano group, a carboxamide group, an alkoxycarbonyl group, or a monovalent group of a substituted or unsubstituted aromatic compound, and R2 represents a hydrogen atom, a C1 to C6 alkyl group, a C1 to C6 alkoxy group, a cyano group or a C1 to C6 acyl group.)

[Chemical Formula 29]

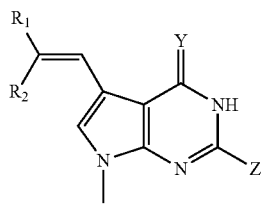

(XIII)

(in Formula XIII, Y represents O, S or NH, Z represents $NH_2$ when Y is O or S, or a hydrogen atom when Y is NH, R1 represents a hydrogen atom, a cyano group, a carboxamide group, an alkoxycarbonyl group, or a monovalent group of a substituted or unsubstituted aromatic compound, and R2 represents a hydrogen atom, a C1 to C6 alkyl group, a C1 to C6 alkoxy group, a cyano group or a C1 to C6 acyl group.)

[Chemical Formula 30]

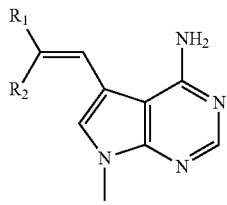

(XIV)

(in Formula XIV, R1 represents a hydrogen atom, a cyano group, a carboxamide group, an alkoxycarbonyl group, or a monovalent group of a substituted or unsubstituted aromatic compound, and R2 represents a hydrogen atom, a C1 to C6 alkyl group, a C1 to C6 alkoxy group, a cyano group or a C1 to C6 acyl group.)

(the group represented by Formula XI is produced from a reaction between the groups that are represented by Formula I and Formula II, the group represented by Formula XII is produced from a reaction between the groups that are represented by Formula III and Formula II, the group represented by Formula XIII is produced from a reaction between the groups that are represented by Formula IV and Formula II, and the group represented by Formula XIV is produced from a reaction between the groups that are represented by Formula V and Formula II, respectively), and a method of manufacturing photoresponsive nucleic acids including the following groups that are represented by Formula XV, Formula XVI, Formula XVII or Formula XVIII as photoresponsive nucleic acids that are produced according to step (b):

[Chemical Formula 31]

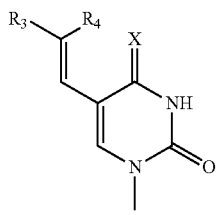

(XV)

(in Formula XV, X represents O, S or NH, R4 represents a hydrogen atom, a C1 to C6 alkyl group, a C1 to C6 alkoxy group, a cyano group or a C1 to C6 acyl group, and R3 represents a monovalent group of a substituted or unsubstituted aromatic compound, a hydrogen atom, a cyano group, a carboxamide group or an alkoxycarbonyl group.)

[Chemical Formula 32]

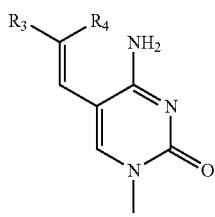

(XVI)

(in Formula XVI, R4 represents a hydrogen atom, a C1 to C6 alkyl group, a C1 to C6 alkoxy group, a cyano group or a C1 to C6 acyl group, R3 represents a monovalent group of a substituted or unsubstituted aromatic compound, a hydrogen atom, a cyano group, a carboxamide group or an alkoxycarbonyl group.)

[Chemical Formula 33]

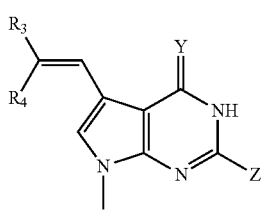

(XVII)

(in Formula XVII, Y represents O, S or NH, Z represents $NH_2$ when Y is O or S, or a hydrogen atom when Y is NH, R4 represents a hydrogen atom, a C1 to C6 alkyl group, a C1 to C6 alkoxy group, a cyano group or a C1 to C6 acyl group, and R3 represents a monovalent group of a substituted or unsubstituted aromatic compound, a hydrogen atom, a cyano group, a carboxamide group or an alkoxycarbonyl group.)

[Chemical Formula 34]

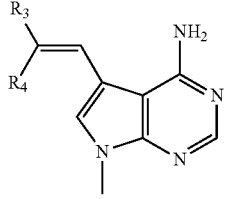

(XVIII)

(in Formula XVIII, R4 represents a hydrogen atom, a C1 to C6 alkyl group, a C1 to C6 alkoxy group, a cyano group or a C1 to C6 acyl group, R3 represents a monovalent group of a substituted or unsubstituted aromatic compound, a hydrogen atom, a cyano group, a carboxamide group or an alkoxycarbonyl group.) (the group represented by Formula XV is produced from a reaction between the groups that are represented by Formula VI and Formula VII, the group represented by Formula XVI is produced from a reaction between the groups that are represented by Formula VIII and Formula VII, the group represented by Formula XVII is produced from a reaction between the groups that are represented by Formula IX and Formula VII, and the group represented by Formula XVIII is produced from a reaction between the groups that are represented by Formula X and Formula VII, respectively).

The reaction in step (a) of the present invention is based on so-called Heck reaction (Mizoroki-Heck reaction), which enables accomplishment of dramatic time shortening and yield improvement compared to the conventional Heck reaction and also enables the post-synthesis of an oligomer of modified nucleic acids which has been impossible before.

The reaction in step (b) of the present invention is based on so-called Suzuki coupling (Suzuki-Miyaura coupling), which enables accomplishment of dramatic time shortening and yield improvement compared to conventional Suzuki coupling and also enables the post-synthesis of an oligomer of modified nucleic acids which has been impossible before.

Therefore, for the reaction of step (a) and step (b) of the present invention, conditions and the compounds (functional groups) which are conventionally used for Heck reaction and Suzuki coupling can be also used, unless specifically described otherwise in the present invention.

As for R1, any group which can be used for Heck reaction as above may be used. In the present invention, it may be generally a hydrogen atom, a cyano group, a carboxamide group, an alkoxycarbonyl group, or a monovalent group of a substituted or unsubstituted aromatic compound, and preferably a hydrogen atom, a cyano group, a carboxamide group, or a C2 to C6 alkoxycarbonyl group. As for the alkoxycarbonyl group, a C2 to C6, preferably C2 to C4 alkoxycarbonyl group may be generally used. Specific examples include a methoxycarbonyl group, an ethoxycarbonyl group, a propoxycarbonyl group and a butoxycarbonyl group. In particular, a methoxycarbonyl group and an ethoxycarbonyl group are preferred. The monovalent group of a substituted or unsubstituted aromatic compound may be a monovalent group of a substituted or unsubstituted heterocyclic compound.

As for R2, any group which can be used for Heck reaction as above may be used. In the present invention, it may be generally a hydrogen atom, a C1 to C6 alkyl group, a C1 to C6 alkoxy group, a cyano group or a C1 to C6 acyl group, and preferably a hydrogen atom, a C1 to C3 alkyl group, a C1 to C3 alkoxy group, a cyano group or a C1 to C3 acyl group.

As for R3, any group which can be used for Suzuki coupling as above may be used. In the present invention, it may be generally a monovalent group of a substituted or unsubstituted aromatic compound, a hydrogen atom, a cyano group, a carboxamide group or an alkoxycarbonyl group, and preferably a monovalent group of a substituted or unsubstituted aromatic compound, a hydrogen atom, a cyano group, a carboxamide group, a C2 to C6 alkoxycarbonyl group. As for the alkoxycarbonyl group, a C2 to C6, preferably C2 to C4 alkoxycarbonyl group may be used. Specific examples include a methoxycarbonyl group, an ethoxycarbonyl group, a propoxycarbonyl group and a butoxycarbonyl group. In particular, a methoxycarbonyl group and ethoxycarbonyl are preferred. The monovalent group of a substituted or unsubstituted aromatic compound may be a monovalent group of a substituted or unsubstituted heterocyclic compound. With respect to R3 group for Suzuki coupling, a bulky group having a wide planar structure may be also used with high efficiency. Specifically, by introducing a group as R3 group for Suzuki coupling, a group which is larger than R1 group for Heck reaction, i.e., a group having a wide planar structure, may be appropriately introduced.

As for R4, any group which can be used for Suzuki coupling as above may be used. In the present invention, it may be generally a hydrogen atom, a C1 to C6 alkyl group, a C1 to C6 alkoxy group, a cyano group or a C1 to C6 acyl group, and preferably a hydrogen atom, C1 to C3 alkyl group, a C1 to C3 alkoxy group, a cyano group or a C1 to C3 acyl group.

According to a preferred embodiment, the monovalent group of a substituted or unsubstituted aromatic compound includes generally 1 to 10, preferably 1 to 8, more preferably 1 to 6, still more preferably 1 to 4, and particularly more preferably 1 to 3 rings, and it may be the monovalent group of a substituted or unsubstituted heterocyclic compound.

According to a preferred embodiment, the monovalent group of a substituted or unsubstituted aromatic compound generally consists of a 4- to 8-membered ring, preferably a 4- to 7-membered ring, more preferably a 4- to 6-membered ring, and still more preferably 5- to 6-membered ring, and it may be the monovalent group of a substituted or unsubstituted heterocyclic compound.

According to a preferred embodiment, the monovalent group of a substituted or unsubstituted aromatic compound includes one to three 5- to 6-membered rings, and a monovalent group in which at least one ring is a heterocyclic ring is used.

According to a preferred embodiment, examples of the monovalent group of a substituted or unsubstituted aromatic compound include a monovalent group of benzene, phentalene, indene, naphthalene, azulene, heptalene, biphenylene, as-indacene, s-indacene, acenaphthylene, fluorene, phenalene, phenanthrene and anthracene.

According to a preferred embodiment, examples of the monovalent group of a substituted or unsubstituted aromatic compound include a monovalent group of furan, benzofuran, isobenzofuran, thiophene, benzothiophene, isobenzothiophene, pyrrole, benzopyrrole and isobenzopyrrole.

According to a preferred embodiment, examples of the monovalent group of a substituted or unsubstituted aromatic compound include furan-2-yl, furan-3-yl, benzofuran-2-yl, benzofuran-3-yl, isobenzofuran-1-yl, isobenzofuran-3-yl, thiophen-2-yl, thiophen-3-yl, benzothiophen-2-yl, benzothiophen-3-yl, isobenzothiophen-1-yl, isobenzothiophen-3-yl, pyrrol-2-yl, pyrrol-3-yl, benzopyrrol-2-yl, benzopyrrol-3-yl, isobenzopyrrol-1-yl, and isobenzopyrrol-3-yl. According to a preferred embodiment, examples of the monovalent group of a substituted or unsubstituted aromatic compound include furan-2-yl, benzofuran-2-yl, thiophen-2-yl, benzothiophen-2-yl, pyrrol-2-yl and benzopyrrol-2-yl.

A1 represents a halogen atom and specific examples include a fluorine atom, a chlorine atom, a bromine atom and an iodine atom. According to a preferred embodiment, examples of the halogen atom for A1 include a bromine atom and an iodine atom. Particularly preferred examples include an iodine atom.

A2 represents a halogen atom and specific examples include a fluorine atom, a chlorine atom, a bromine atom and an iodine atom. According to a preferred embodiment, examples of the halogen atom for A2 include a bromine atom and an iodine atom. Particularly preferred examples include a bromine atom.

Step (a) and step (b) are carried out by microwave heating in the presence of a metal catalyst, a basic substance, and a solvent.

In the present invention, shortening of reaction time and improvement of yield are achieved simultaneously by heating by microwaves.

Heating by microwaves is generally carried out to obtain the temperature range of 70 to 140° C., preferably 75 to 125° C., more preferably 80 to 120° C., and still more preferably 80 to 110° C. The heating by microwaves is carried out at said temperature generally for the time period of 1 to 30 minutes, preferably 2 to 20 minutes, more preferably 3 to 20 minutes, and still more preferably 3 to 10 minutes. The heating by microwaves may be carried out in two or at least three divided steps. The frequency of magnetron that is used for a microwave may be any one which can provide the temperature and time described above. In general, frequency of 2.45 GHz may be used. The power of microwave may be any one which can provide the temperature and time described above.

As for the metal catalyst, a metal catalyst which can be used for Heck reaction and Suzuki coupling may be used. In particular, a palladium complex catalyst is preferred. Examples of a palladium complex catalyst which may be suitably used include a $PdCl_4$ catalyst and $Pd(OAc)_2$ catalyst, etc.

As for the solvent, a solvent which can be used for Heck reaction and Suzuki coupling may be used. In particular, an aprotic polar solvent is preferred. Examples of an aprotic polar solvent which may be suitably used include acetone, acetonitrile, N,N-dimethylformamide (DMF) and dimethyl sulfoxide (DMSO). Preferably, DMF and DMSO may be used. These aprotic polar solvents may be used with addition of water.

As for the basic substance, a basic substance which can be used for Heck reaction and Suzuki coupling may be used. (Examples of a basic substance which may be suitably used) include trialkylamine. Examples of trialkylamine include trialkylamine having a C1 to C6 alkyl group, preferably trialkylamine having a C1 to C4 alkyl group, and more preferably trialkylamine having a C2 to C4 alkyl group. According to the preferred embodiment, trimethylamine, triethylamine, tripropylamine and tributylamine may be used. Preferably, triethylamine and tributylamine may be used.

According to the preferred embodiment, step (a) and step (b) are carried out by heating by microwaves in the presence of a metal catalyst, a basic substance, a solvent, and a substance for activating the reaction. With heating by microwaves in the presence of a substance for activating the reaction, reaction of step (a) and step (b) may be carried out in a particularly preferable way.

As for the substance for activating the reaction which may be used for the present invention, an aqueous solution of carboxylate may be mentioned. Examples of carboxylate include C1 to C3 carboxylate, and preferably acetate may be used. Examples of the carboxylate include an alkali metal salt, preferably a sodium salt or a potassium salt, and more preferably a sodium salt may be used.

The aqueous solution of carboxylate is preferably a buffer solution having pH range of 4.5 to 6.0, and more preferably pH 5.0 to 5.5. The buffer solution may be prepared by further adding carboxylic acid to the carboxylate dissolved in water.

According to the preferred embodiment of the present invention, the aqueous solution of carboxylate may be used both as a basic substance and a substance for activating the reaction.

EXAMPLES

Herein below, the present invention is explained in detail in view of the Examples. However, the present invention is not limited to the Examples.

Synthesis of a Photoresponsive Compound from 5-iodo-2'-deoxyuridine ($^{I}$U)

Synthesis of a photoresponsive compound with high yield within a short period of time was carried out by efficient heating using microwaves. For this, multiple kinds of a substrate having a vinyl group as shown in the Scheme 1 were tested.

Scheme (1)

[Chemical Formula 35]

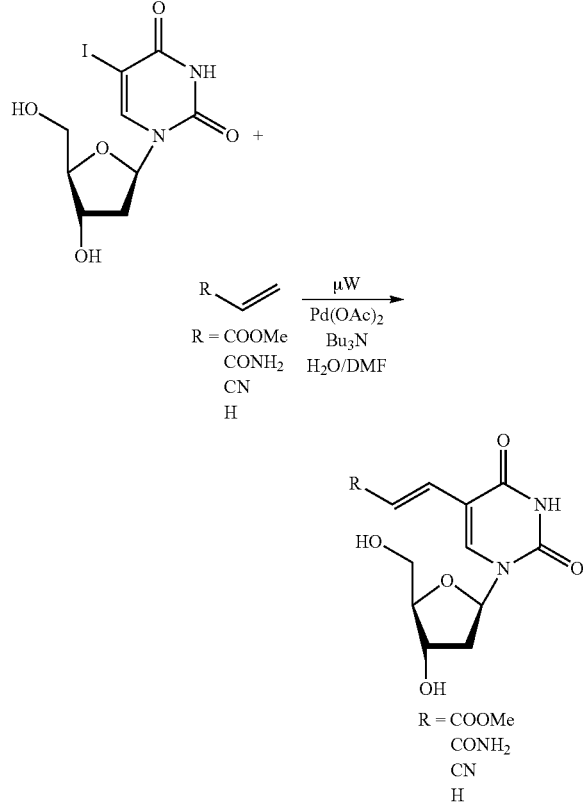

Example 1

(1) Synthesis of 5-carbomethoxyvinyl-2'-deoxyuridine ($^{CV}$U)

The Compound ($^{CV}$U) Shown in FIG. 1 was Synthesized according to the Scheme (1). Under nitrogen atmosphere, palladium (II) acetate (13.4 mg, 0.06 mmol) was dissolved in DMF (500 μL) and added with 5-iodo-2'-deoxyuridine (200 mg, 0.56 mmol) as powder itself to give a suspension. Furthermore, tributylamine (130 μL, 0.56 mmol) and methylacrylate (120 μL, 1.12 mmol) were also added thereto. After the addition of the reagents, the mixture was heated to 100° C. by irradiation of microwaves and reacted for 4 minutes. The sample obtained after the completion of the reaction was filtered to remove palladium powder and the solvent was removed by using an evaporator. Purification was carried out by using a silica gel column. The solvent for elution was varied from $CHCl_3$:MeOH=95:5 to 9:1 to obtain a product as a white solid (162 mg, 0.52 mmol, 92%). From the results of $^1$H NMR analysis, it was identified as 5-carbomethoxyvinyl-2'-deoxyuridine ($^{CV}$U), i.e., the compound shown in FIG. 1.

$^1$H NMR (DMSO 300 MHz) δ11.6 (br. s, 1H, 3NH); 8.42 (s, 1H, H—C (6)); 7.38 (d, 1H, J=16.2 Hz, CH=CH); 6.86 (d, 1H, J=16.2 Hz, CH=CH); 6.14 (t, 1H, J=6.3, H—C(1')); 5.26 (d, 1H J=4.2 Hz, 3'-OH); 5.17 (t, 1H, J=5.4 Hz, 5'-OH); 4.26 (m, 1H, H—C(3')); 3.81 (dd, 1H, J=6.6, 3.3 Hz, H—C(4')); 3.69 (s, 3H, OMe); 3.63-3.59 (m, 2H, H—C(5')); 2.21-2.16 (m, 2H, H—C(2')). HRMS (MALDI) cald. for $C_{13}H_{17}N_2O_7$ [(M+H)$^+$]: 313.104, found: 313.333.

Example 2

(2) Synthesis of 5-carbamoylvinyl-2'-deoxyuridine ($^{CMV}$U)

Figure 2:
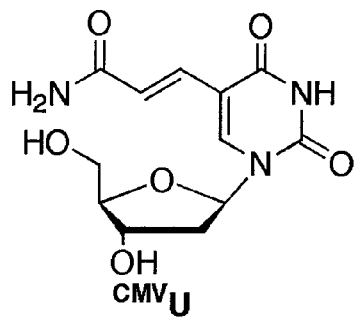
FIG. 2 is a drawing showing the structural formula of $^{CMV}U$.

The compound ($^{CMV}$U) shown in FIG. 2 was synthesized according to the Scheme (1). Under nitrogen atmosphere, palladium (II) acetate (13.4 mg, 0.06 mmol) was dissolved in DMF (500 μL) and added with 5-iodo-2'-deoxyuridine (200 mg, 0.56 mmol) as powder itself to give a suspension. Furthermore, tributylamine (130 μL, 0.56 mmol) and acrylamide (100 mg, 1.40 mmol) were also added thereto. After the addition of the reagents, the mixture was heated to 100° C. by irradiation of microwaves and reacted for 4 minutes. The sample obtained after the completion of the reaction was filtered to remove palladium powder and the solvent was removed by using an evaporator. The resultant was washed with the solvent of $CHCl_3$:MeOH=1:1 to obtain a product as a white solid (141 mg, 0.48 mmol, 85%). From the results of $^1$H NMR analysis, it was identified as 5-carbamoylvinyl-2'-deoxyuridine ($^{CMV}$U), i.e., the compound shown in FIG. 2.

$^1$H NMR (DMSO 300 MHz) δ11.5 (br. s, 1H, 3NH); 8.28 (s, 1H, H—C (6); 7.50 (br. s, 1H, $NH_2$); 6.91 (br. s, 1H, $NH_2$); 7.12 (d, 1H, J=15.6 Hz, CH=CH); 6.97 (d, 1H, J=15.6 Hz, CH=CH); 6.14 (t, 1H, J=6.3, H—C(1')); 5.25 (d, 1H, J=4.2 Hz, 3'-OH); 5.16 (t, 1H, J=5.1 Hz, 5'-OH); 4.26 (m, 1H, H—C(3')); 3.81 (m, 1H, H—C(4')); 3.66-3.59 (m, 2H, H—C (5'); 2.21-2.09 (m, 2H, H—C(2')).

HRMS (MALDI) cald. for $C_{12}H_{15}N_3O_6Na$ [(M+Na)$^+$]: 320.086, found: 320.502.

Example 3

(3) Synthesis of 5-cyanovinyl-2'-deoxyuridine ($^{CNV}$U)

Figure 3:
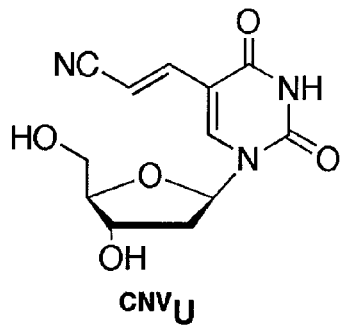
FIG. 3 is a drawing showing the structural formula of $^{CNV}U$.

The compound ($^{CNV}$U) shown in FIG. 3 was synthesized according to the Scheme (1). Under nitrogen atmosphere, palladium (II) acetate (13.4 mg, 0.06 mmol) was dissolved in DMF (500 μl) and added with 5-iodo-2'-deoxyuridine (200 mg, 0.56 mmol) as powder itself to give a suspension. Furthermore, tributylamine (130 μL, 0.56 mmol) and acrylonitrile (91 μL, 1.40 mmol) were also added thereto. After the addition of the reagents, the mixture was heated to 100° C. by irradiation of microwaves and reacted for 4 minutes. The sample obtained after the completion of the reaction was filtered to remove palladium powder and the solvent was removed by using an evaporator. Purification was carried out by using a silica gel column. The solvent for elution was varied from CHCl$_3$:MeOH=95:5 to 9:1 to obtain a product as a white solid (82 mg, 0.31 mmol, 54%). From the results of $^1$H NMR analysis, it was identified as 5-carbomethoxyvinyl-2'-deoxyuridine ($^{CNV}$U), i.e., the compound shown in FIG. 3.

$^1$H NMR (DMSO 300 MHz) δ11.7 (br. s, 1H, 3NH); 8.35 (s, 1H, H—C (6)); 7.23 (d, 1H, J=16.2 Hz, CH=CH); 6.52 (d, 1H, J=16.2 Hz, CH=CH); 6.10 (t, 1H, J=6.0, H—C(1')); 5.27 (d, 1H, J=4.2 Hz, 3'-OH); 5.11 (t, 1H, J=5.4 Hz, 5'-OH); 4.25 (m, 1H, H—C(3')); 3.82 (dd, 1H, J=7.2, 3.6 Hz, H—C(4')); 3.68-3.57 (m, 2H, H—C(5')); 2.20-2.15 (m, 2H, H—C(2')).

HRMS (MALDI) cald. for C$_{12}$H$_{13}$N$_3$O$_6$Na [(M+Na)$^+$]: 302.075, found: 302.067.

Example 4

(4) Synthesis of 5-vinyl-2'-deoxyuridine ($^V$U)

Figure 4:
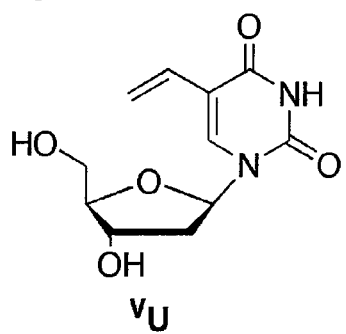
FIG. 4 is a drawing showing the structural formula of $^{V}U$.

The compound ($^V$U) shown in FIG. 4 was synthesized according to the Scheme (1). Under nitrogen atmosphere, palladium (II) acetate (13.4 mg, 0.06 mmol) was dissolved in DMF (500 μL) and added with 5-iodo-2'-deoxyuridine (200 mg, 0.56 mmol) as powder itself to give a suspension. Furthermore, tributylamine (130 μL, 0.56 mmol) and methylacrylate (1.04 mL, 11.3 mmol) were also added thereto. After the addition of the reagents, the mixture was heated to 100° C. by irradiation of microwaves and reacted for 20 minutes. The sample obtained after the completion of the reaction was filtered to remove palladium powder and the solvent was removed by using an evaporator. Purification was carried out by using a silica gel column. The solvent for elution was varied from CHCl$_3$:MeOH=95:5 to 9:1 to obtain a product as a white solid (80 mg, 0.31 mmol, 56%). From the results of $^1$H NMR analysis, it was identified as 5-vinyl-2'-deoxyuridine ($^V$U), i.e., the compound shown in FIG. 4.

$^1$H NMR (DMSO 300 MHz) δ11.4 (br. s, 1H, 3NH); 8.11 (s, 1H, H—C (6)); 6.36 (dd, 1H, J=17.7, 11.5 Hz, CH=CH); 6.15 (t, 1H, J=6.3, H—C(1')); 5.82-5.78 (m, 1H, vinyl cis); 5.26-5.09 (m, 3H, vinyl trans, 3'-OH, 5'-OH); 4.25 (t, 1H, J=4.0 Hz, H—C(3')); 3.79-3.78 (m, 1H, H—C(4')); 3.65-3.54 (m, 2H, H—C(5')); 2.18-2.10 (m, 2H, H—C(2')).

HRMS (MALDI) cald. for C$_{11}$H$_{14}$N$_2$O$_5$Na [(M+Na)$^+$]: 277.080, found: 277.066.

[Summary 1]

The yield and time for the reactions of the Examples 1 to 4 above and the yield and time for each reaction that is carried out by conventional method (i.e., Comparative examples 1 to 4) are summarized in Table 1 below.

[Chemical Formula 36]

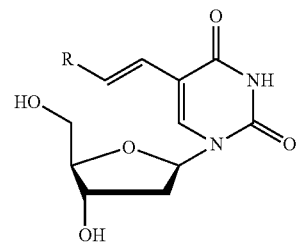

TABLE 1

| Entry | R | Conventional method | Microwave |
|---|---|---|---|
| 1 | COOMe ($^{CV}$U) | For 120 minutes 65% | For 4 minutes 98% |
| 2 | CONH$_2$ ($^{CMV}$U) | — | For 4 minutes 85% |
| 3 | CN ($^{CNV}$U) | For 180 minutes 70% | For 4 minutes 54% |
| 4 | H ($^V$U) | For 1500 minutes 56% | For 20 minutes 56% |

According to the method of the present invention, the reaction time was shortened up to 1/75 and the yield was increased by 30% compared to the conventional method. Furthermore, there are lots of side reactions in the conventional method. However, according to the present invention, the side reactions were also decreased significantly.

Synthesis of a Photoresponsive Nucleic Acid from Oligodeoxynucleotide (ODN) having 5-iodo-2'-deoxyuridine ($^I$U)

Post-synthesis of a photoresponsive nucleic acid from oligodeoxynucleotide (ODN) having 5-iodo-2'-deoxyuridine ($^I$U) was carried out.

Synthesis of ODN Having $^I$U

ODN1 ($^I$U) (5'-$^I$UTTTTT-3') or ODN2 ($^I$U) (5'-$^I$UGCGTGA-3') was synthesized by using ABI 3400 DNA synthesizer. Without performing separation from a support using an aqueous ammonia solution, it was obtained as CPG.

Example 5

Post-synthesis of ODN Having 5-cyanovinyl-2'-deoxyuridine ($^{CNV}$U)

Post-synthesis of ODN having 5-cyanovinyl-2'-deoxyuridine ($^{CNV}$U) was carried out according to the Scheme (2).

Scheme (2)

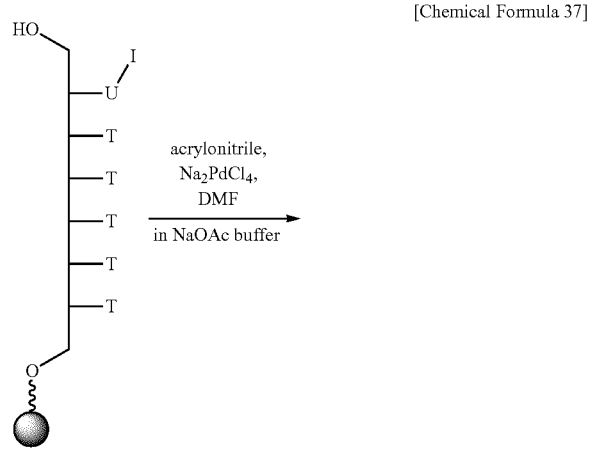

[Chemical Formula 37]

Figure 5:
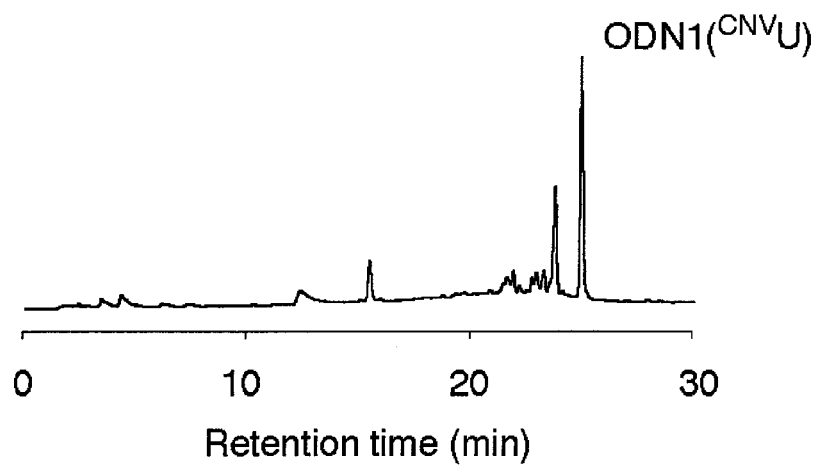
FIG. 5 is a drawing showing the HPLC chart.

0.1 M sodium acetate butter solution (180 µL, pH=5.2) was added to ODN1 ($^I$U)-CPG (2 mg, approximately 100 nmol loading), further added with DMF solution (180 µL) of acrylonitrile (12 mg, 226 µmol) and DMF solution (180 µL) of Na PdCl$_4$ (5.8 mg, 20 µmol), and then the reaction solution was heated at 80° C. for 10 minutes by using microwaves. The supernatant solution was removed and washed four times with DMF (250 µL×4). To the reaction mixture, 0.1 M sodium acetate butter solution (180 µL, pH=5.2) was further added, DMF solution (180 µL) of acrylonitrile (12 mg, 226 µmol) and DMF solution (180 µL) of Na$_2$PdCl$_4$ (5.8 mg, 20 µmol) were added thereto, and then the reaction solution was heated at 80° C. for 10 minutes by using microwaves. The supernatant solution was removed and washed four times with DMF (250 µL×4). By using an aqueous ammonia solution (300 µL), separation from the support was carried out by incubation at room temperature for 12 hours. After removing ammonia by using SpeedVac, the HPLC analysis was carried out (FIG. 5). HPLC conditions (elution with a solvent mixture of 50 mM ammonium formate, pH 7.0, linear gradient over 30 min from 3% to 20% acetonitrile, detection at 300 nm). Peaks derived from ODN1 ($^{CNV}$U) were fractionated and measured with MALDI-TOF-MS. calcd. for ODN1($^{CNV}$U):[(M+H)$^+$] 1801.22, found 1801.46.

From the results of MALDI-TOF-MS analysis, successful post-synthesis of ODN was confirmed.

Example 6

Post-synthesis of ODN Having 5-carbamoylvinyl-2'-deoxyuridine ($^{CV}$U)

5-carbamoylvinyl-2'-deoxyuridine ($^{CV}$U) was synthesized according to the Scheme (3).

Scheme (3)

[Caption Formula 38]

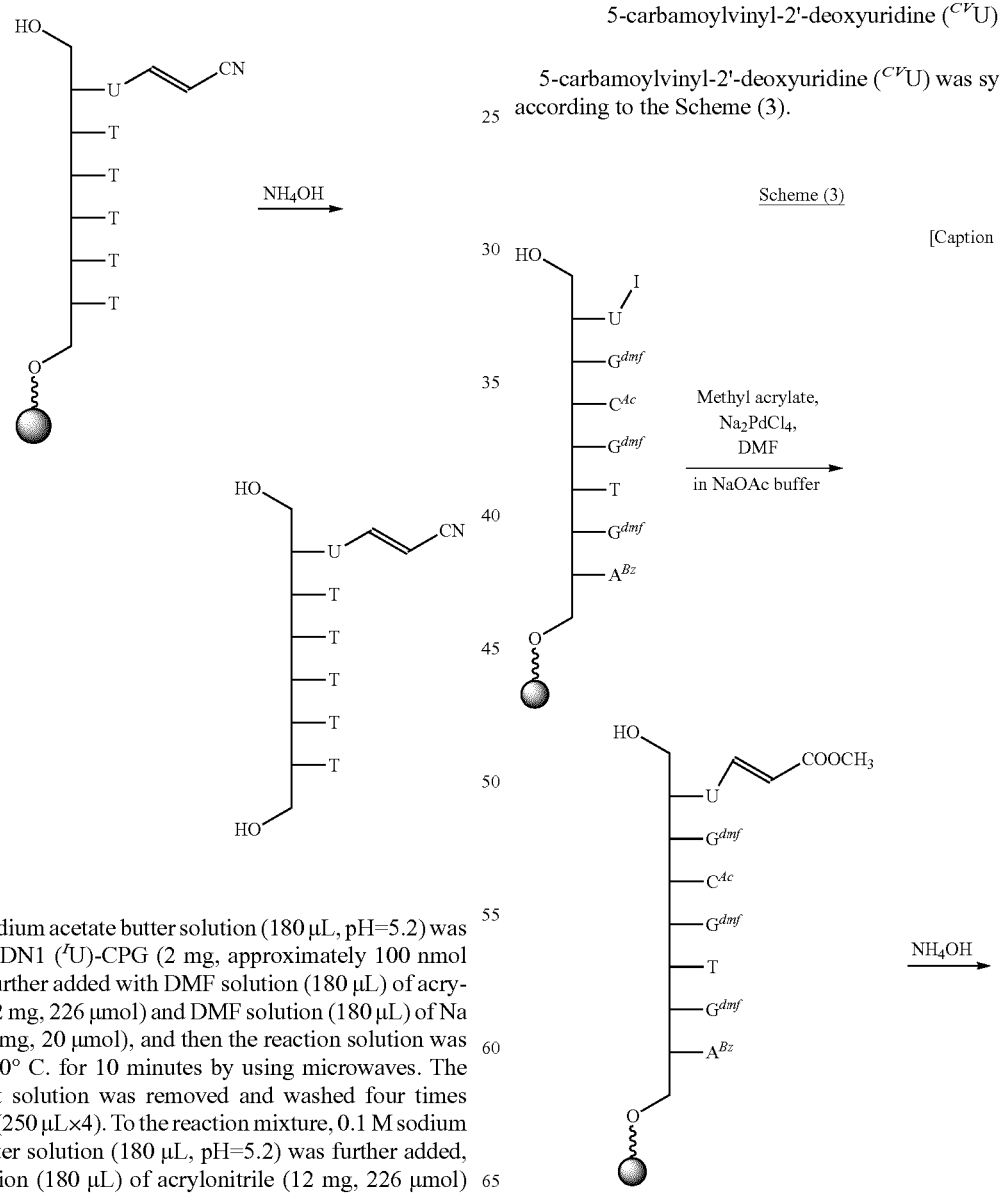

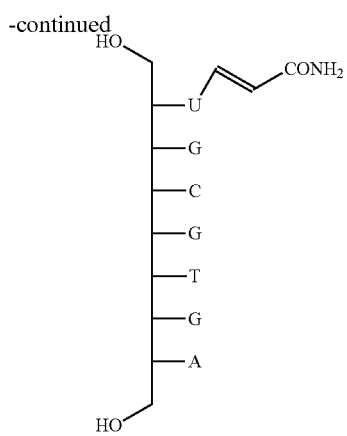

Figure 6:
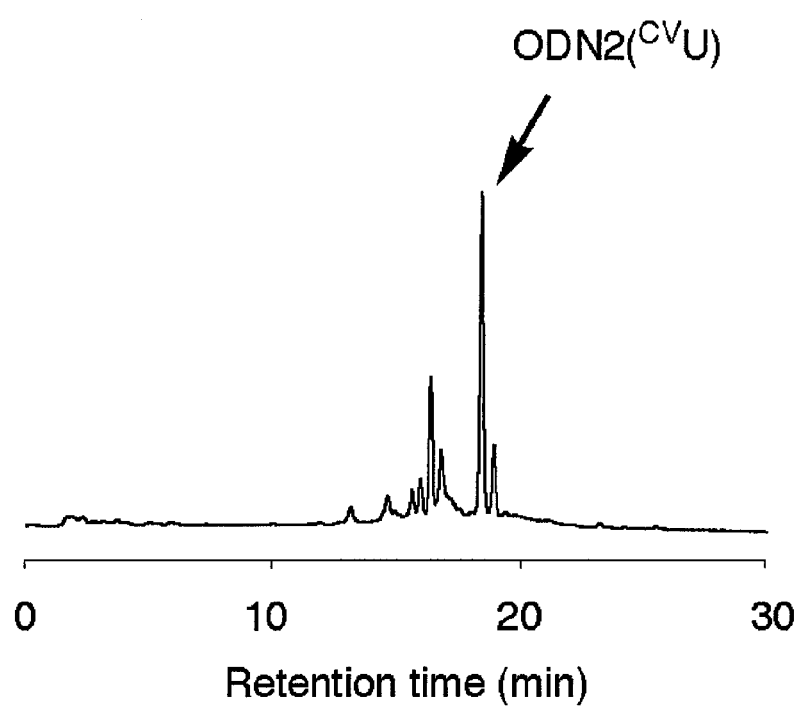
FIG. 6 is a drawing showing the HPLC chart.

0.1 M sodium acetate butter solution (180 μL, pH=5.2) was added to ODN2 ($^I$U)-CPG (2 mg, approximately 100 nmol loading), further added with DMF solution (180 μL) of methylacrylate (19.5 mg, 226 μmol) and DMF solution (180 μl) of Na PdCl$_4$ (5.8 mg, 20 μmol), and then the reaction solution was heated at 80° C. for 10 minutes by using microwaves. The supernatant solution was removed and washed four times with DMF (500 μL×4). The same procedure was repeated for the resulting reaction mixture. The supernatant solution was removed and washed four times with DMF (500 μL×4) and four times with H$_2$O (500 μL×4). With respect to the reaction mixture, separation from the support was carried out using an aqueous ammonia solution (500 μL) by incubating at 55° C. for 10 hours. After removing ammonia by using SpeedVac, the HPLC analysis was carried out (FIG. 6). HPLC conditions (elution with a solvent mixture of 50 mM ammonium formate, pH 7.0, linear gradient over 30 min from 3% to 20% acetonitrile, detection at 320 nm). Peaks derived from ODN2 ($^{CV}$U) were fractionated and measured with MALDI-TOF-MS.

calcd. for ODN2 ($^{CV}$U): [(M+H)$^+$] 2192.47, found 2192.51.

From the results of MALDI-TOF-MS analysis, successful post-synthesis of ODN including A, G, C or T was also confirmed.

Synthesis of a Photoresponsive Nucleic Acid from Oligodeoxynucleotide (ODN) having 5-bromovinyl-2'-deoxyuridine ($^{BrV}$U)

Example 7

Post-Synthesis of ODN Having 5-vinylfuran-2'-deoxyuridine

Post-synthesis of ODN having 5-vinylfuran-2'-deoxyuridine was carried out according to the Scheme (4).

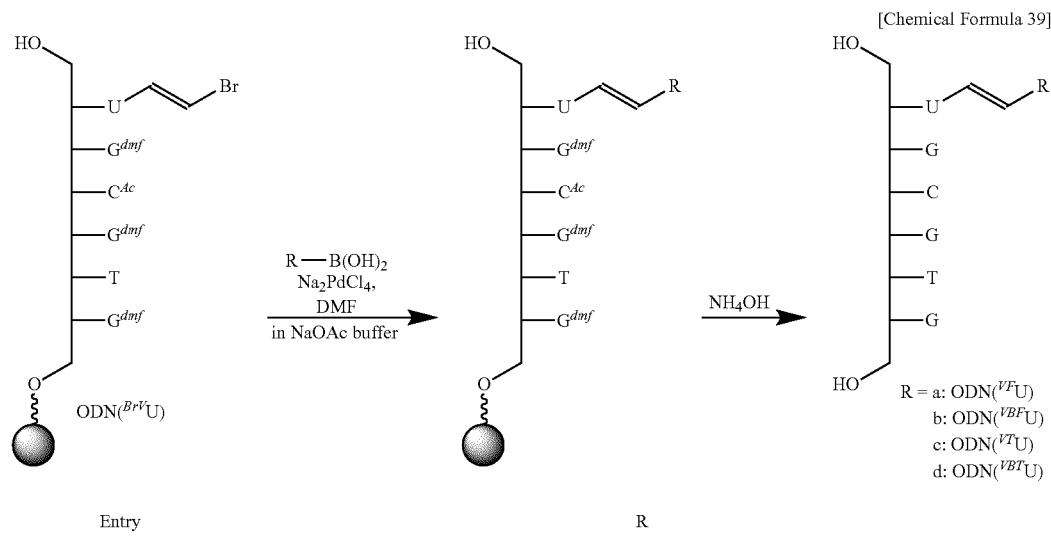

Scheme (4)

d 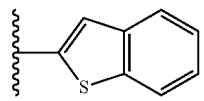

Figure 7:
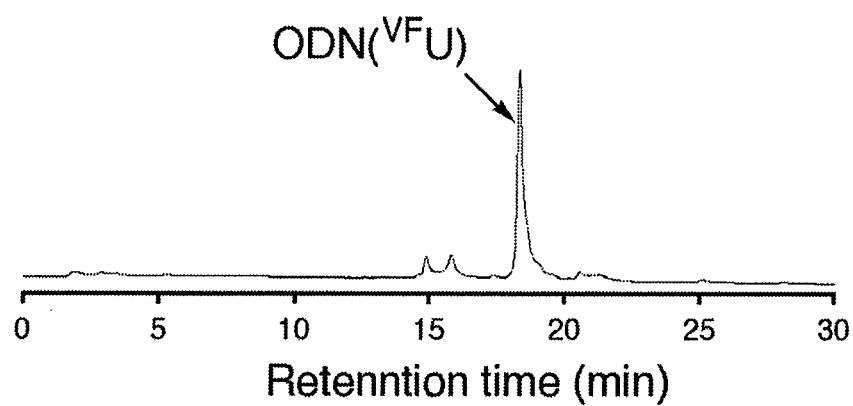
FIG. 7 is a drawing showing the HPLC chart.

DMF (150 μL), 2-furan boronic acid (44.8 mg, 400 μmol), PdCl$_2$(PPh$_3$)$_2$ (14.0 mg, 20 μmol) and triethyl amine (100 μL) were added in the order to ODN ($^{BrV}$U)-CPG (2 mg, approximately 100 nmol loading), and then the reaction solution was heated at 100° C. for 10 minutes by using microwaves. The supernatant solution was removed and washed four times with DMF (500 μL×4) and four times with H$_2$O (500 μL×4). The transparent solution and the aqueous washing solution were admixed with each other. To the CPG obtained after the reaction, an aqueous ammonia solution (500 μL) was added, and separation from the support was carried out by incubation at 65° C. for 4 hours. After removing ammonia by using SpeedVac, the HPLC analysis was carried out (FIG. 7). HPLC conditions (elution with a solvent mixture of 50 mM ammonium formate, pH 7.0, linear gradient over 30 min from 3% to 20% acetonitrile, detection at 350 nm).

Mass analysis was carried out by MALDI-TOF-MS, and as a result, a data corresponding to the mass of the target compound, i.e., ODN ($^{VF}$U) was obtained.

calcd. for ODN($^{VF}$U):[(M+H)$^+$] 1902.30, found 1902.85

Example 8

Post-synthesis of ODN having 5-vinylbenzofuran-2'-deoxyuridine

Post-synthesis of ODN having 5-vinylbenzofuran-2'-deoxyuridine was carried out.

Figure 8:
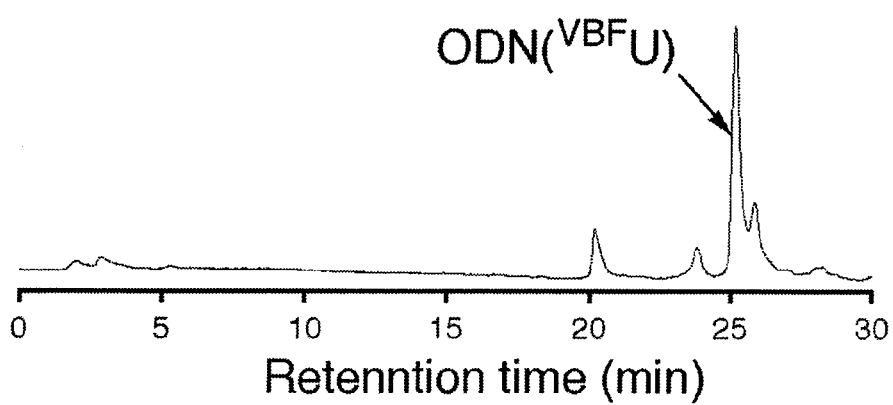
FIG. 8 is a drawing showing the HPLC chart.

DMF (150 μL), 2-benzofuran boronic acid (64.8 mg, 400 μmol), PdCl$_2$(PPh$_3$)$_2$ (14.0 mg, 20 μmol) and triethyl amine (100 μL) were added in this order to ODN ($^{BrV}$U)-CPG (2 mg, approximately 100 nmol loading), and then the reaction solution was heated at 100° C. for 10 minutes by using microwaves. The supernatant solution was removed and washed four times with DMF (500 μL×4) and four times with H$_2$O (500 μL×4). The transparent solution and the aqueous washing solution were admixed with each other. To the CPG obtained after the reaction, an aqueous ammonia solution (500 μL) was added, and separation from the support was carried out by incubation at 65° C. for 4 hours. After removing ammonia by using SpeedVac, the HPLC analysis was carried out (FIG. 8).

9 corresponds to the mass analysis based on MALDI-TOF MS of ODN including $^{VBF}$U as a sample in a crude state, which has been synthesized before and analyzed by HPLC. As a result, a data corresponding to the mass of the target compound, i.e., ODN ($^{VBF}$U), was obtained.

calcd. for ODN($^{VBF}$U):[(M+H)$^+$] 1952.36, found. 1952.05

Example 9

Post-synthesis of ODN Having 5-vinylthiophene-2'-deoxyuridine

Post-synthesis of ODN having 5-vinylthiophene-2'-deoxyuridine was carried out according to the Scheme (4).

DMF (150 μL), 2-thiophen boronic acid (51.2 mg, 400 μmol), PdCl$_2$(PPh$_3$)$_2$ (14.0 mg, 20 μmol) and tri-ethyl amine (100 μL) were added in this order to ODN ($^{BrV}$U)-CPG (2 mg, approximately 100 nmol loading), and then the reaction solution was heated at 100° C. for 10 minutes by using microwaves. The supernatant solution was removed and washed four times with DMF (500 μL×4) and four times with H$_2$O (500 μL>4). The transparent solution and the aqueous washing solution were admixed with each other. To the CPG obtained after the reaction, an aqueous ammonia solution (500 μl) was added, and separation from the support was carried out by incubation at 65° C. for 4 hours. After removing ammonia by using SpeedVac, purification was carried out by HPLC.

Mass analysis was carried out based on MALDI-TOF-MS, and as a result, a data corresponding to the mass of the target compound, i.e., ODN ($^{VT}$U) having 5-vinylthiophen-dU, was obtained.

calcd. for ODN ($^{VT}$U): [(M+H)$^+$] 1916.33, found 1916.77

Example 10

Post-synthesis of ODN Having 5-vinylbenzothiophene-2'-deoxyuridine

Post-synthesis of ODN having 5-vinylbenzothiophene-2'-deoxyuridine was carried out according to the Scheme (4).

DMF (150 μL), 2-tbenzothiophen boronic acid (71.2 mg, 400 μmol), PdCl$_2$(PPh$_3$)$_2$ (14.0 mg, 20 μmol) and triethyl amine (100 μL) were added in this order to ODN ($^{BrV}$U)-CPG CPG (2 mg, approximately 100 nmol loading), and then the reaction solution was heated at 100° C. for 10 minutes by using microwaves. The supernatant solution was removed and washed four times with DMF (500 μL×4) and four times with H$_2$O (500 μL×4). The transparent solution and the aqueous washing solution were admixed with each other. To the CPG obtained after the reaction, an aqueous ammonia solution (500 μL) was added, and separation from the support was carried out by incubation at 65° C. for 4 hours. After removing ammonia by using SpeedVac, purification was carried out by HPLC.

Mass analysis was carried out based on MALDI-TOF-MS, and as a result, a data corresponding to the mass of the target compound, i.e., ODN ($^{VT}$U) having 5-vinylthiophen-dU, was obtained.

calcd. for $^{ODN}$($^{VBF}$U): [(M+H)$^+$] 1967.34, found 1967.20

[Summary 2]

According to the post-synthetic method of the Example 5 to 10 above, various photoresponsive nucleic acids can be manufactured in a day. On the contrary, according to conventional synthesis of photoresponsive nucleic acids based on a phosphoroamidite process, as a time for synthesis, about a week or so is required for any kind of photoresponsive nucleic acids.

The invention claimed is:
1. A

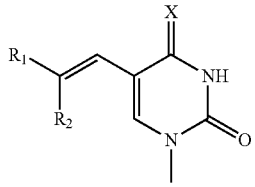
(XI)

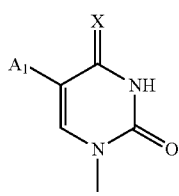
(I)

(II)

method of manufacturing a nucleic acid having a group represented by the following Formula XV:

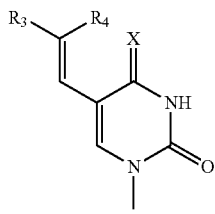
(XV)

in the Formula XV, X represents O, S or NH, R4 represents a hydrogen atom, a C1 to C6 alkyl group, a C1 to C6 alkoxy group, a cyano group or a C1 to C6 acyl group, and
R3 represents a monovalent group of a substituted or unsubstituted aromatic compound, or a cyano group, wherein the method comprises the following step (b):
(b) reacting a nucleic acid having a base sequence comprising a nucleotide base moiety represented by Formula VI with a compound represented by Formula VII in the presence of a palladium complex catalyst, a basic substance and a solvent by microwave heating:

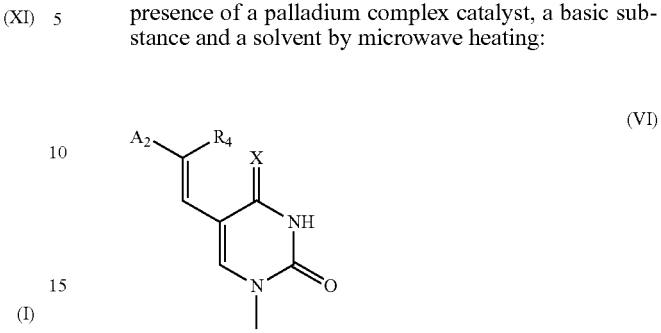
(VI)

in the Formula VI, X represents O, S or NH,
R4 represents a hydrogen atom, a C1 to C6 alkyl group, a C1 to C6 alkoxy group, a cyano group or a C1 to C6 acyl group, and
A2 represents a halogen atom;

$$R_3-B(OH)_2 \quad (VII)$$

in the Formula VII, R3 represents a monovalent group of a substituted or unsubstituted aromatic compound, or a cyano group.

2. The method according to claim 1, wherein the step (b) is carried out by heating by microwaves in the presence of a palladium complex catalyst, a basic substance, a solvent, and an aqueous solution of carboxylate.

3. The method according to claim 1, wherein the basic substance is trialkylamine having a C1 to C6 alkyl group.

4. The method according to claim 1, wherein the step (b) is carried out by heating by microwaves in the presence of a palladium complex catalyst, a solvent, and an aqueous solution of carboxylate.

5. The method according to claim 2, wherein the aqueous solution of carboxylate is an aqueous solution of an alkali metal salt of C1 to C3 carboxylic acid.

6. The method according to claim 2, wherein the aqueous solution of carboxylate is a buffer solution having a pH range of 4.5 to 6.0.

7. The method according to claim 1, wherein the heating by microwaves is carried out in the temperature range of 70 to 140° C.

8. The method according to claim 1, wherein the heating by microwaves is carried out in the time range of 1 to 30 minutes.

9. The method according to claim 1, wherein the solvent is an aprotic polar solvent.

* * * * *